United States Patent [19]

Hohenschutz et al.

[11] 4,314,947

[45] Feb. 9, 1982

[54] PROCESS FOR COMPLETING THE ESTERIFICATION OF CARBOXYLIC ACIDS WITH ALCOHOLS

[75] Inventors: Heinz Hohenschutz, Mannheim; Josef Gnad, Ludwigshafen; Güenter Dinkhauser, Limburgerhof; Eberhard Schaefer, Ludwigshafen, all of Fed. Rep. of Germany

[73] Assignee: BASF Aktiengesellschaft, Fed. Rep. of Germany

[21] Appl. No.: 971,662

[22] Filed: Dec. 21, 1978

[51] Int. Cl.$^3$ .................... C07C 67/08; C07C 67/54
[52] U.S. Cl. .................... 260/410; 202/158; 203/60; 203/63; 203/67; 203/69; 203/99; 203/DIG. 6; 260/410.6; 260/410.9 R; 260/421; 560/231; 560/248; 560/263; 560/265
[58] Field of Search .................... 560/231, 265–266, 560/263–264, 256, 204, 248; 260/410.9 R, 421, 410, 410.6; 203/DIG. 6, 99, DIG. 16, 60, 63, 67, 69

[56] References Cited

U.S. PATENT DOCUMENTS 2,274,061  2/1942  Hawby .................... 560/265

OTHER PUBLICATIONS

Chemie Ingenieur Technik, 43 (1971) pp. 1001–1007.

*Primary Examiner*—Vivan Garner
*Attorney, Agent, or Firm*—Keil & Witherspoon

[57] ABSTRACT

A process for completing the esterification of aliphatic carboxylic acids of 1 to 8 carbon atoms with aliphatic or cycloaliphatic alcohols of 3 to 10 carbon atoms at the boiling point of the alcohol in a column operated with bottom heating, the lower space of the column being free from fitments, the middle space being provided with a packing and the upper space being provided with a packing or other fitments, in which process the water of esterification is driven off at the top of the column by azeotropic distillation, the starting mixture is fed into the side of the column from 5 to 10 m above the liquid level, the ester formed is taken off as liquid from the column bottom, and the column is operated with flooding such that the liquid level is from 6 to 10 m, with the liquid mixture filling the lower column space, which is free from fitments, and the lower part of the packed layer above the said space.

4 Claims, 1 Drawing Figure

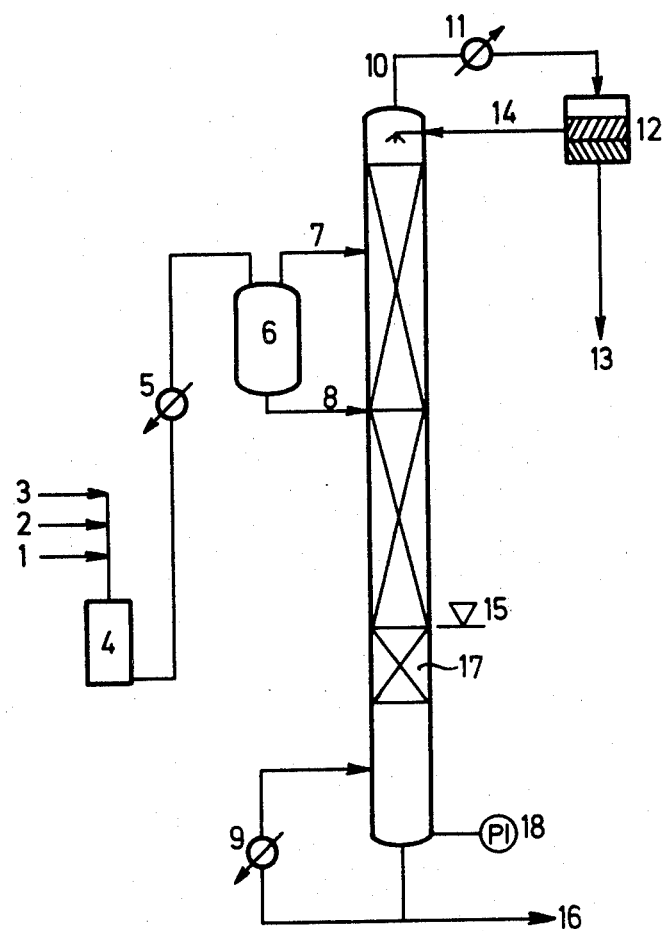

PROCESS FOR COMPLETING THE ESTERIFICATION OF CARBOXYLIC ACIDS WITH ALCOHOLS

The present invention relates to a novel continuous process for completing the esterification of carboxylic acids with alcohols.

The manufacture of carboxylic acid esters from aliphatic carboxylic acids and alcohols by heating the starting materials in the presence of a catalyst is known. The industrial esterification of lower aliphatic carboxylic acids is carried out with continuous removal of the water formed during the reaction. The crude ester thereby obtained is as a rule neutralized with an aqueous alkali and then subjected to a refining distillation.

According to a process for the continuous manufacture of carboxylic acid esters described in Chemie-Ingenieur-Technik 43 (1971), 1001, the starting materials are reacted in the presence of a catalyst in an esterifying column which consists of a reaction section below the feed point, and a rectifying section. The water is distilled off azeotropically at the top. The rectifying section serves to remove the organic acid from the rising water azeotrope. The crude ester is taken off as vapor just above the bottom of the esterifying column. It still contains excess alcohol which is distilled off as the light fraction in the downstream pure ester column.

Since the esterification is carried out in the presence of an acid catalyst, e.g., sulfuric acid or p-toluenesulfonic acid, and since water is formed during esterification, corrosion of the metallic materials of the reaction vessels, e.g., reaction kettles or columns, is observed when manufacturing carboxylic acid esters industrially; this corrosion interferes with undisturbed continuous long-term operation. These difficulties arise particularly under conditions which aim at complete conversion of the reactants.

It is an object of the present invention to provide a process which permits the manufacture of the carboxylic acid esters to be carried out with substantially complete conversion of the reactants and substantial suppression of corrosion of the esterification apparatus, and thereby allows trouble-free long-term operation during carboxylic acid ester production.

We have found that this object is achieved by the present invention, which relates to a process for completing the esterification of aliphatic carboxylic acids of 1 to 8 carbon atoms with aliphatic or cycloaliphatic alcohols of 3 to 10 carbon atoms by treating a mixture which in addition to the carboxylic acid ester already formed contains as yet unconverted proportions of carboxylic acid and alcohol, together with an esterifying catalyst and water of reaction, and with or without an entraining agent, at the boiling point of the alcohol or of the entraining agent, in a column operated with bottom heating, the water of esterification being driven off at the top of the column by azeotropic distillation, wherein the lower space of the column is free from fitments, the middle space of the column is provided with a packing and the upper space of the column is provided with a packing or other fitments, the starting mixture is fed into the side of the column from 5 to 10 m above the liquid level, the ester formed is taken off as liquid from the column bottom, and the column is operated with flooding such that the liquid level is from 6 to 10 m, with the liquid mixture filling the lower column space, which is free from fitments, and the lower part of the packed layer above the said space.

The esters obtainable by the novel process are formed from carboxylic acids of 1 to 8 carbon atoms and alcohols of 3 to 10 carbon atoms. Examples of suitable acids are acetic acid, propionic acid, butyric acid and ethylhexanoic acid. Examples of suitable alcohols are aliphatic and cycloaliphatic monohydric and polyhydric alcohols, e.g., propanol, butanol, pentanol, ethylhexanol, methylglycol, ethylglycol, butylglycol and p-tert.-butylcyclohexanol. These starting materials are as a rule employed in the stoichiometric amount. However, the alcohol or acid can also be employed in an excess of up to 50% over the stoichiometric amount.

The catalysts used are conventional esterification catalysts, for example, non-oxidizing mineral acids, e.g., sulfuric acid, hydrochloric acid or phosphoric acid, or organic sulfonic acids, e.g., benzenesulfonic acid, methanesulfonic acid and p-toluenesulfonic acid.

Entraining agents are as a rule only employed if the crude ester formed, or any excess alcohol employed, has insufficient water-entraining character, if any. Examples of suitable entraining agents are isobutyl acetate, n-butyl acetate, benzene, chlorobenzene, dichloroethane and butanol.

The process according to the invention is used to complete the esterification of the above starting materials, i.e., the process of the invention starts from a mixture which has been obtained from the starting materials in a conventional esterification apparatus, e.g., a stirred kettle, reaction still or delay-time vessel, at from 50° to 200° C. This mixture contains, for example, from 10 to 30 percent by weight of the carboxylic acid, from 10 to 30 percent by weight of the alcohol, from 50 to 80 percent by weight of the carboxylic acid ester obtained from the said carboxylic acid and the said alcohol, from 2 to 15 percent by weight of water and from 0.05 to 3 percent by weight of an esterifying catalyst, with or without an entraining agent.

The complete esterification is carried out in a column which is operated with bottom heating and which is free from fitments in the lower space of the column. This lower space occupies the lowest 4-6 m of the total height of the column which is, for example, 20-28 m. The middle space of the column is provided with a packing. The lower part of this layer of packing is covered by the liquid reaction mixture. The upper part of the layer of packing, which extends from the upper liquid level to the height of the feed point of the starting mixture (stripping section) comprises from about 7 to 11 plates. The upper space of the column, upwards from the feed point of the starting mixture (the rectifying section), which is also provided with a packing or with other fitments, such as bubble-cap valve trays or perforated trays, comprises from about 9 to 14 plates. The inner diameter of the columns is from about 80 to 120 cm.

Using the novel process, the pre-esterified mixture is introduced, advantageously at the boiling point of the alcohol or of the entraining agent and under atmospheric, superatmospheric or reduced pressure, but preferably under atmospheric pressure, into the side of the middle space of the column, above the liquid level. Water and entraining agent are driven off through the top of the column. The crude ester formed is obtained from the liquid mixture at the bottom of the column. By controlling the crude ester offtake, the liquid level in the column is kept at 6-10 m. The level maintained is such that the liquid mixture completely fills the lower column space, which is free from fitments, and part of the layer of packing above the said space. Advantageously 1–6 m, preferably 3–5 m, of the layer of packing are covered by the liquid.

Using the process according to the invention, the manufacture of the carboxylic acid ester can be carried out continuously on an industrial scale, and even after years of operation only slight signs of corrosion are observed. This advantageous effect is presumably due to the fact that the water content in the liquid crude ester mixture in the column does not exceed 0.05 percent by weight in the process according to the invention. Since such an advantageous low water content is not obtained if the lower part of the column is not flooded and instead the liquid level in the column is kept—for example in accordance with the process described in Chem. Ing. Techn. 43(1971), 1001—below the upper tube sheet of the circulatory evaporator, or if the liquid level is set to some other height, the advantageous result achieved by using the novel process must be considered surprising.

The process of the invention is carried out, as illustrated in the FIGURE, in, for example, a column having a height of 24 m and a diameter of 90 cm. The lower column space is free from fitments up to a height of 500 cm. The reaction space above it is packed. The esterification mixture feed point, in the side of the column, is 15 m above the lower end of the column. The section of the column below the feed point (the stripping section) comprises 10 plates and the section above the feed point (the rectifying section) comprises 11 plates.

Butanol (1), acetic acid (2) and sulfuric acid (3) are introduced continuously into a mixing vessel (4). The mixture of the starting materials, pre-heated by means of a heat exchanger (5), is pre-esterified at about 90° C. in a reaction chamber (6) upstream from the column, and part of the water of esterification which is formed is introduced as steam into the upper part of the column (7). The pre-esterified mixture is passed through the line (8) into the esterifying column, heated by a natural-circulation evaporator (9). The temperature in the column is about 110° C.

At the top of the column, an azeotrope of water, alcohol and ester is taken off through line (10) and condensed (11). The distillate collected in the receiver (12) forms two phases. The aqueous lower phase is removed through line (13) for further working up, and the organic upper phase is passed through line (14), as reflux, to the top of the column. The liquid level (15) in the bottom of the reaction column is kept at a height of 6–10 m by controlling the amount of crude ester run off (16). The upper liquid level extends 400 cm into the lower layer of packing (17). The liquid level in the column is advantageously monitored by measuring the static pressure PI (18) at the bottom end of the column. It is also possible to measure the pressure difference between the top and bottom parts of the esterifying column. The crude ester taken off the column is thereafter processed in the conventional manner, i.e., it is neutralized, washed and rectified.

EXAMPLE 1

A mixture obtained by mixing 2,165 parts/h of acetic acid, 3,135 parts/h of n-butanol and 64 parts/h of sulfuric acid, and heating to 90° C., is passed into the column shown in the FIGURE and described above. The mixture contains 60 percent by weight of butyl acetate, 18 percent by weight of acetic acid, 14 percent by weight of n-butanol, 6.8 percent by weight of water and 1.2 percent by weight of sulfuric acid.

The water of esterification is continuously removed from the system at the top of the column. The bottom temperature is 143° C. At the top of the column, the temperature assumes a value of 92° C. The liquid level in the column is kept at 850 cm by setting the static pressure in the bottom to 1.63 bar. The upper liquid level extends 400 cm into the lower layer of packing. The crude ester taken off the column contains 0.031% of water and has an acid number of 10.6 mg of KOH/g of product.

EXAMPLE 2

Using the method described in Example 1, 1,487 parts/h of acetic acid, 2,158 parts/h of iso-butanol and 46.8 parts/h of sulfuric acid are introduced into the pre-esterification stage. The esterification mixture passed into the column contains 60 percent by weight of isobutyl acetate, 15 percent by weight of iso-butanol, 18 percent by weight of acetic acid, 5.7 percent by weight of water and 1.3 percent by weight of sulfuric acid. The bottom temperature is 133° C. At the top of the column, the temperature assumes a value of 90° C. The liquid level in the column is kept at 8.80 m by setting the static pressure in the bottom to 1.65 bar. The crude ester taken off contains 0.05 percent by weight of water and has an acid number of 10.2 mg of KOH/g of product.

EXAMPLE 3

Using the method described in Example 1, 696 parts/h of acetic acid, 1,184 parts/h of ethylene glycol monoethyl ether, 783 parts/h of iso-butyl acetate (to act as the entraining agent) and 17.1 parts/h of sulfuric acid are passed via the pre-esterification stage into the column. The pre-esterified mixture contains 43.8 percent by weight of glycol acetate, 13.3 percent by weight of ethylene glycol monoethyl ether, 10.1 percent by weight of acetic acid, 29.2 percent by weight of isobutyl acetate, 3.0 percent by weight of water and 0.6 percent by weight of sulfuric acid.

The bottom temperature is 142° C. The temperature at the top of the column assumes a value of 88° C. The liquid level is brought to 8.0 m by setting the static pressure in the bottom to 1.8 bar. The water of esterification is continuously removed from the system, together with the entraining agent, at the top of the column. The crude ester obtained contains 0.035 percent by weight of water and has an acid number of 12 mg of KOH/g of product.

We claim:
1. A continuous process for completing the esterification of aliphatic carboxylic acids of 1 to 8 carbon atoms with aliphatic or cycloaliphatic alcohols of 3 to 10 carbon atoms by treating a pre-esterified reaction mixture which in addition to the carboxylic acid ester already formed contains as yet unconverted proportions of carboxylic acid and alcohol, together with an esterifying catalyst and water of reaction, and with or without an entraining agent, at the boiling point of the alcohol or of the entraining agent, in a column operated with bottom heating, the water of esterification being driven off at the top of the column by azeotropic distillation, wherein the lower space of the column is free from fitments, the middle space of the column is provided with a packing and the upper space of the column is provided with a packing or other fitments, the starting pre-esterified reaction mixture is fed into the middle space of the column from 5 to 10 m above the upper liquid level, which upper liquid level is maintained within the lower portion of the packing in said middle space, the ester formed is taken off as liquid from the column bottom, and the column is operated with flooding such that the upper liquid level is from 6 to 10 m above the bottom of said lower space, with the liquid mixture filling said lower space and said lower portion of said packing in said middle space.

2. A process as claimed in claim 1, wherein the starting mixture contains from 10 to 30 percent by weight of carboxylic acid, from 10 to 30 percent by weight of the alcohol, from 50 to 80 percent by weight of the ester of the carboxylic acid and the alcohol, from 2 to 15 percent by weight of water and from 0.05 to 3 percent by weight of an esterifying catalyst, with or without an entraining agent.

3. A process as claimed in claim 1, wherein the height of the column is 20–28 m, the internal diameter of the column is 80–120 cm, and the lower space of the column, which is free from fitments, has a height of 4–6 m, the upper part of the layer of packing, which extends from the upper liquid level to the height of the feed point of the starting mixture, comprises 7–11 plates and the upper space of the column, from the feed point of the starting mixture upwards, comprises 9–14 plates.

4. A process as claimed in claim 1, wherein 1–6 m of the packed layer in the column, immediately above the lower column space which is free from fitments, is filled by the liquid mixture.

* * * * *